United States Patent [19]

Chang et al.

[11] Patent Number: 4,990,663
[45] Date of Patent: Feb. 5, 1991

[54] PROCESS FOR PREPARING HALOGENATED AROMATIC AMINES

[75] Inventors: Yu-Wei Chang, Wilmington, Del.; Robert L. Seagraves, Pennsville, N.J.

[73] Assignee: E. I Du Pont de Nemours and Company, Wilmington, Del.

[21] Appl. No.: 351,696

[22] Filed: May 15, 1989

[51] Int. Cl.$^5$ .................. C07C 209/00; C07C 227/44
[52] U.S. Cl. ........................................ 564/5; 562/456; 564/417
[58] Field of Search ...................... 564/5, 417; 562/456

[56] References Cited

U.S. PATENT DOCUMENTS 2,509,891  5/1950  Starr, Jr. et al. .................. 260/578
3,145,231  8/1964  Kosak ................................. 260/580
4,070,401  1/1978  Hirai et al. ........................ 260/580
4,212,824  7/1980  Seagraves ......................... 260/580

FOREIGN PATENT DOCUMENTS 0525487  2/1977  Japan .
52-35651  9/1977  Japan .

Primary Examiner—Richard L. Raymond
Assistant Examiner—Peter G. O'Sullivan

[57] ABSTRACT

This invention relates to a process for the hydrogenation of halogenated aromatic nitro compounds to the corresponding halogenated amines using a platinum catalyst in the presence of certain aminoalkyl ethers or alkanolamines. It relates in addition to halogenated aromatic amines containing an amount of such aminoalkyl ether or alkanolamine effective to stabilize said halogenated aromatic amine. The storage stabilizers and dehalogenation inhibitors contain a total of 2 to 6 carbon atoms and can be represented by the formula:

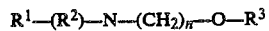

$$R^1-(R^2)-N-(CH_2)_n-O-R^3$$

wherein $R^1$ and $R^2$ may be the same or different —H or —CH$_2$CH$_2$OH, n is an integer from 2 to 3, and $R^3$ is either —H or —CH$_3$.

9 Claims, No Drawings

PROCESS FOR PREPARING HALOGENATED AROMATIC AMINES

FIELD OF THE INVENTION

This invention relates to a process for the hydrogenation of halogenated aromatic nitro compounds to the corresponding halogenated amines using a platinum catalyst in the presence of certain aminoalkyl ethers or alkanolamines. It relates also to halogenated aromatic amines containing an amount of such aminoalkyl ether or alkanolamine effective to stabilize said halogenated aromatic amine.

BACKGROUND OF THE INVENTION

It is recognized in the art that extensive dehalogenation may take place in the catalytic hydrogenation of halogenated nitroaromatics. Dehalogenation not only leads to less pure product but the acidic by-product hydrogen halides corrode the hydrogenation equipment. One approach to the problem has been to use special catalysts, but such catalysts can be expensive to prepare and are sometimes less active than the commonly used catalysts, as in French Patent No. 1,417,236. The other approach has been the addition of dehalogenation inhibitors to the hydrogenation. Kosak, in U.S. Pat. No. 3,145,231, describes the advantageous use of cycloaliphatic amines such as piperazine, morpholine and their N-substituted alkyl derivatives, as dehalogenation inhibitors in the hydrogenation of halogenated nitroaromatics using a platinum catalyst. Harai et. al. in U.S. Pat. No. 4,070,401, disclose the use of alkylamines, alicyclic amines and polyalkylenepolyamines, all having pKbs of less than 4.2, as useful dehalogenation inhibitors in the platinum-catalyzed hydrogenation of similar halogenated nitroaromatics. These additives while moderately effective dehalogenation inhibitors, allow a relatively high degree of dehalogenation when the hydrogenation of dihalogenated nitroaromatics is conducted neat, i. e., without a solvent. Mitsui Toatsu JP 52-35651 discloses the use of ammonia, alkanolamines and piperidines as dehalogenation inhibitors in the hydrogenation of halogenated nitroaromatics using a palladium catalyst. In the patent examples, dehalogenation levels ranged from 0.2 to 1.0% and higher. Mitsui Toatsu JP 52-5487 discloses the hydrogenation of halogenated nitroaromatics using a nickel catalyst in the presence of alkylamines, alkanolamines, heterocyclic bases or alicyclic amines. Methanol was used as a solvent in all of the examples. Dehalogenation was reported in the relatively high range of 0.1 to 0.8%. While the above dehalogenation inhibitors are useful, still better ones would be desirable.

BRIEF SUMMARY OF THE INVENTION

The present invention relates to certain alkanolamines and their methyl ethers which are superior dehalogenation inhibitors in the hydrogenation of halogenated nitroaromatics using a platinum catalyst. The dehalogenation inhibitors are also effective storage stabilizers for the product halogenated aromatic amines.

DETAILED DESCRIPTION OF THE INVENTION

The dehalogenation inhibitors and storage stabilizers of the present invention comprise low molecular weight alkanolamines and related amino ethers. They may be defined as compounds containing a total of 2 to 6 carbon atoms and having the formula:

$$R^1—(R^2)—N—(CH_2)_n—O—R^3$$

wherein $R^1$ and $R^2$ may be the same or different —H or —CH$_2$CH$_2$OH, n is an integer from 2 to 3, and $R^3$ is either —H or —CH$_3$.

Typical examples include ethanolamine, 1-amino-2-propanol, 3-amino-1-propanol, 2-methoxyethylamine, 3-methoxy-1-propylamine, diethanolamine and triethanolamine. Ethanolamine and 2-methoxyethylamine are the preferred inhibitors because of their dehalogenation inhibition efficiencies. Ethanolamine is most preferred because of price and its better efficiency at higher temperatures.

The amount of dehalogenation inhibitor charged to the hydrogenation depends on the nitroaromatic to be reduced and the reaction conditions. Concentrations of from 0.1 to 2.0 weight percent based on nitroaromatic may be used. Lower amounts may not be effective or marginally so, and higher amounts while effective would not the economic. The preferred concentration range is between 0.25 and 1.0%. The most preferred range is 0.5 to 0.8%.

If the corresponding nitroaromatic can be obtained, almost any halogenated aromatic amine may be prepared by the method of this invention. Halogenated aromatic amines that can be manufactured include but are not limited to: halogenated anilines such as o-, m- or p-chloroaniline, m-bromoaniline, p-fluoroaniline, 2,3-, 2,4-, 2,5- and 3,4-dichloroanilines; halogenated aminophenols such as 3-bromo-, 3-chloro- and 3-fluoro-4-aminophenols and 2,3-dichloro-4-aminophenol; halogenated biphenylamines such as 4-fluoro-, 4-chloro- or 4-bromo-3'-biphenylylamines; alkyl halogenated anilines such as 4-chloro-2-aminotoluene; and halogenated aminophenyl carboxylic acids such as 6-chloro-2-aminobenzoic acid.

The catalyst used in the method of this invention may be any of the commonly used platinum hydrogenation catalysts. It may consist essentially of the metal itself but it preferably should be on a support. Well-known examples of supports are various forms of carbon, alumina and diatomaceous earth. The catalyst may also be promoted by other metals such as iron, nickel or chromium. The preferred catalyst of this invention is the iron-promoted platinum catalyst supported on oleophilic carbon black described by Seagraves in U.S. Pat. No. 4,212,824.

Usually sufficient catalyst is added to the hydrogenation of this invention to afford rapid rates of hydrogen absorption and consequent reduction of the nitroaromatic to amine. Catalyst concentration may therefore vary from 10,000 to 150,000 parts by weight of nitroaromatic to platinum. The preferred range is 50,000 to 125,000 with 75,000 to 100,000 being most preferred.

The hydrogenation of this invention may be run at temperatures of 80° to 200° C. with temperatures of 120° to 180° C. preferred and 135° to 160° C. most preferred. Pressures may range from 200 to 1200 psig with 400 to 800 psig preferred and 500 to 600 psig most preferred.

The superior performance of the dehalogenation inhibitors of this invention was demonstrated in a laboratory semi-continuous reactor, as described in Examples 1–7 & Control A. In a semi-continuous reactor, a measured amount of halogenated nitroaromatic, such as 3,4-dichloro-1-nitrobenzene, and hydrogen were fed simultaneously at about 135° to 160° C. to a heel of product amine, the candidate inhibitor, catalyst and by-product water which simulates the reaction mass and effluent from a continuous reactor.

EXAMPLE 1

To a one liter Parr titanium autoclave equipped with an agitator, cooling coil, thermowell, electrical heater, hydrogen feed system and system for introducing molten nitroaromatic under pressure, were charged 243 g of 3,4-dichloro-aniline, 54 g of deionized water, 2 g of ethanolamine (0.4 weight % and 1.2 mole % based on nitroaromatic) and catalyst containing 7.9 mg of platinum on carbon modified with 18 mg of iron as iron oxide and/or hydroxide. The autoclave was sealed, the air was displaced with nitrogen and the autoclave was pressure tested. The nitrogen was replaced with hydrogen and the contents of the autoclave were heated to 80° C. The agitation was started and the contents of the autoclave were heated to 100° C. The pressure control regulator on the hydrogen feed was set at 540 psig and this pressure maintained in the autoclave throughout the reduction. The addition of 510 g of 3,4-dichloro-1-nitrobenzene crude (containing 11% 2,3- and 1% 2,5- isomers) was started. During the simultaneous feeding of the hydrogen and the nitroaromatic, the temperature was allowed to rise to 135° C. where it was controlled by the automated cooling water system. The addition of the nitroaromatic was completed in about 120 minutes. About 5 minutes thereafter hydrogen absorption ceased. Heating at reaction conditions was continued for an additional 15 minutes. The autoclave was cooled, the hydrogen was displaced with nitrogen and the organic phase was separated. Analyses by gas phase chromatography indicated that dechlorination, i.e., the total of aniline and monochloroanilines in the product calculated as p-chloroaniline, was less than 235 ppm.

EXAMPLES 2-7 and Control A

Examples 2 through 7 and Control A were carried out in fashion similar to Example 1. Control A presents dechlorination results obtained with the art inhibitor morpholine. Results are given in Table 1.

TABLE 1

| Example Number | Inhibitor Compound | Mole %* | Dechlor ppm** |
|---|---|---|---|
| 2 | 1-amino-2-propanol | 1.5 | 470 |
| 3 | 3-amino-1-propanol | 2.0 | 423 |
| 4 | 2-methoxyethylamine | 2.0 | 282 |
| 5 | 3-methoxy-1-propylamine | 2.5 | 438 |
| 6 | diethanolamine | 2.1 | 344 |
| 7 | triethanolamine | 2.5 | 423 |
| Control A | morpholine | 2.1 | 548 |

*Based on moles of nitroaromatic.
**Based on weight of product amine.

The results from the seven examples described above, indicate that the alkanolamines and related ethers of this invention are superior to morpholine as dehalogenation inhibitors at the levels of inhibitor and catalyst loadings tested in the semi-continuous pilot unit.

The criterion given in U.S. Pat. No. 4,070,401 for the selection of suitable dehalogenation inhibitors, namely that the pKb be less than 4.2 provides inadequate guidance. In fact, the majority of the instant dehalogenation inhibitors have pKbs (per literature data) greater than 4.2 as shown in Table 2.

TABLE 2

| Inhibitor | pKb |
|---|---|
| ethanolamine | 4.5 |
| 2-methoxyethylamine | 4.6 |
| triethanolamine | 6.1 |
| diethanolamine | 5.0 |
| 1-amino-3-propanol | 4.1 |

Evaluation of dehalogenation inhibitors is more typically conducted in batch rather than semi-continuous experiments. When ethanolamine was evaluated in the laboratory batch hydrogenator at 96° C. as a dehalogenation inhibitor at concentrations of nitroaromatic/inhibitor/catalyst considered close to optimum for the same hydrogenation in the semicontinuous unit, hydrogen take-up was slow and erratic, and the reduction did not go to completion even though dehalogenation was very low. In contrast to this, when 2-methoxyethylamine was evaluated under the similar conditions, it was found to have no adverse effect on rate of reduction and to be a good dehalogenation inhibitor being approximately equivalent to morpholine. Further experimentation with ethanolamine showed that if its concentration was lowered and the concentration of catalyst and the temperature was raised, favorable results could be obtained in the laboratory batch hydrogenator.

Examples 8-10 are given in illustration of laboratory batch reductions.

EXAMPLE 8

To a one liter Parr titanium autoclave equipped with an agitator, a cooling coil, a thermowell, an electrical heater and a hydrogen feed system were charged 400 g of 3,4-dichloro-1-nitrobenzene crude, 2 g of ethanolamine (0.5 weight % based on nitroaromatic) and catalyst containing 7.9 mg of platinum on carbon modified with 18 mg of iron as iron oxide and/or hydroxide. The autoclave was sealed, the air was displaced with nitrogen and the autoclave was pressure tested. The nitrogen was replaced with hydrogen and the contents of the autoclave were heated to 75° C. The agitation was started and the pressure control regulator on the hydrogen feed was set to a maximum of 500 psig. As hydrogen was absorbed, the temperature of the reduction mass rose to 96° C. where it was controlled by the automated cooling system. At the end of 188 minutes, hydrogen was still being absorbed but at a very slow rate. The reduction was terminated. The autoclave was cooled, the hydrogen was displaced with nitrogen and the organic phase was separated. Analyses by gas phase chromatography indicated that unreduced nitroaromatic was found to be 8.8%, an unacceptable amount. However dechlorination, i.e., the total of aniline and monochloroanilines in the product calculated as p-chloroaniline, was only 0.03%.

EXAMPLE 9

Example 8 was repeated using 0.375 weight % of ethanolamine based on nitroaromatic, and catalyst containing 15.8 mg of platinum modified with 36 mg of iron. Hydrogenation temperature was controlled at 110° C. instead of 96° C. Hydrogen take-up was faster than in Example 8 and essentially stopped in 100 minutes. The product amine contained only 0.003% dechlorinated derivatives and 0.38% nitroaromatic.

EXAMPLE 10

Example 8 was repeated using 4 g (1.0 weight percent based on nitroaromatic) of 2-methoxyethylamine instead of ethanolamine. Hydrogen absorption was rapid and the reduction time was 148 minutes. The product amine contained 0.05% dechlorinated derivatives and 0.02% residual nitroaromatic.

EXAMPLE 11

The dehalogenation inhibitors of this invention are also effective storage stabilizers for halogenated aromatic amines. Their utility in that connection is demonstrated by this Example.

Round bottom drying ampuls of 20 ml capacity were dried by heating and were then cooled under nitrogen. Ten ml of test samples consisting of molten 3,4-dichloroaniline containing candidate stabilizers were pipetted into the ampuls which were sealed under nitrogen and stored in a 110° C. oven. Periodically an ampul of each sample was removed from the oven and evaluated. Results are recorded in Table 3.

TABLE 3

| Additive | Wt. % | Time, days | Color | High Boilers Weight % |
|---|---|---|---|---|
| None | — | 3 | Red | 0.04 |
| None | — | 60 | Black | 0.19 |
| Ethanolamine | 0.35 | 3 | Lt yellow | 0.02 |
| Ethanolamine | 0.35 | 60 | Yellow | 0.07 |
| 2-methoxyethylamine | 0.43 | 7 | Lt yellow | 0.05 |
| 2-methoxyethylamine | 0.43 | 60 | Yellow | 0.07 |

We claim:

1. A composition consisting essentially of 3,4-dichloroaniline plus an amount effective to stabilize said dichloroaniline of ethanolamine, 1-amino-2-propanol, 3-amino-1-propanol, 2-methoxyethylamine, 3-methoxy-1-propyl-amine, diethanolamine or triethanolamine.

2. The composition of claim 1 wherein said amino compound is ethanolamine.

3. The composition of claim 1 wherein said amino compound is 2-methoxyethylamine.

4. In a process for minimizing the formation of dechlorinated products during the preparation of 3,4-dichloroaniline by the platinum-catalyzed hydrogenation of 3,4-dichloro-1-nitrobenzene, the improvement consisting essentially of hydrogenating 3,4-dichloro-1-nitrobenzene in the presence of ethanolamine, 1-amino-2-propanol, 3-amino-1-propanol, 2-methoxyethylamine, 3-methoxy-1-propyl-amine, diethanolamine or triethanolamine.

5. The process of claim 4 wherein said amino compound is ethanolamine.

6. The process of claim 4 wherein said amino compound is 2-methoxyethylamine.

7. A process for imparting storage stability to 3,4-dichloroaniline consisting essentially of adding thereto an amount effective to stabilize said dichloroaniline of ethanolamine, 1-amino-2-propanol, 3-amino-1-propanol, 2-methoxyethylamine, 3-methoxy-1-propyl-amine, diethanolamine or triethanolamine.

8. The process of claim 7 wherein said amine is ethanolamine.

9. The process of claim 7 wherein said amine is 2-methoxyethylamine.

* * * * *